United States Patent [19]

Thornton

[11] Patent Number: 5,080,105

[45] Date of Patent: Jan. 14, 1992

[54] CARDIOVASCULAR MONITORING SYSTEM

[76] Inventor: William E. Thornton, 701 Coward's Creek Rd., Friendswood, Tex. 77546

[21] Appl. No.: 554,549

[22] Filed: Jul. 19, 1990

[51] Int. Cl.$^5$ ............................................... A61B 5/02
[52] U.S. Cl. .................................... 128/670; 128/715; 128/710; 128/782
[58] Field of Search ............... 128/670, 706, 715, 668, 128/707, 782, 710

[56] References Cited

U.S. PATENT DOCUMENTS

| | | | |
|---|---|---|---|
| 4,803,996 | 2/1989 | Peel et al. | 128/715 |
| 4,827,943 | 5/1989 | Bornn et al. | 128/668 |
| 4,830,021 | 5/1989 | Thornton | 128/707 |
| 4,883,063 | 11/1989 | Bernard et al. | 128/706 |
| 4,889,123 | 12/1989 | Lee | 128/706 |

Primary Examiner—Francis Jaworski
Assistant Examiner—George Manuel

[57] ABSTRACT

A relatively simple and practical system for detecting, recording, and processing physical and emotional parameters affecting the cardiovascular system of a subjects simultaneously with the recording of the subject's EKG data. On replay, should EKG abnormalities be detected, the record is analyzed for physical activities, emotional stresses, and environmental parameters which could cause such abnormalities, so that the appropriate treatment may be selected.

17 Claims, 3 Drawing Sheets

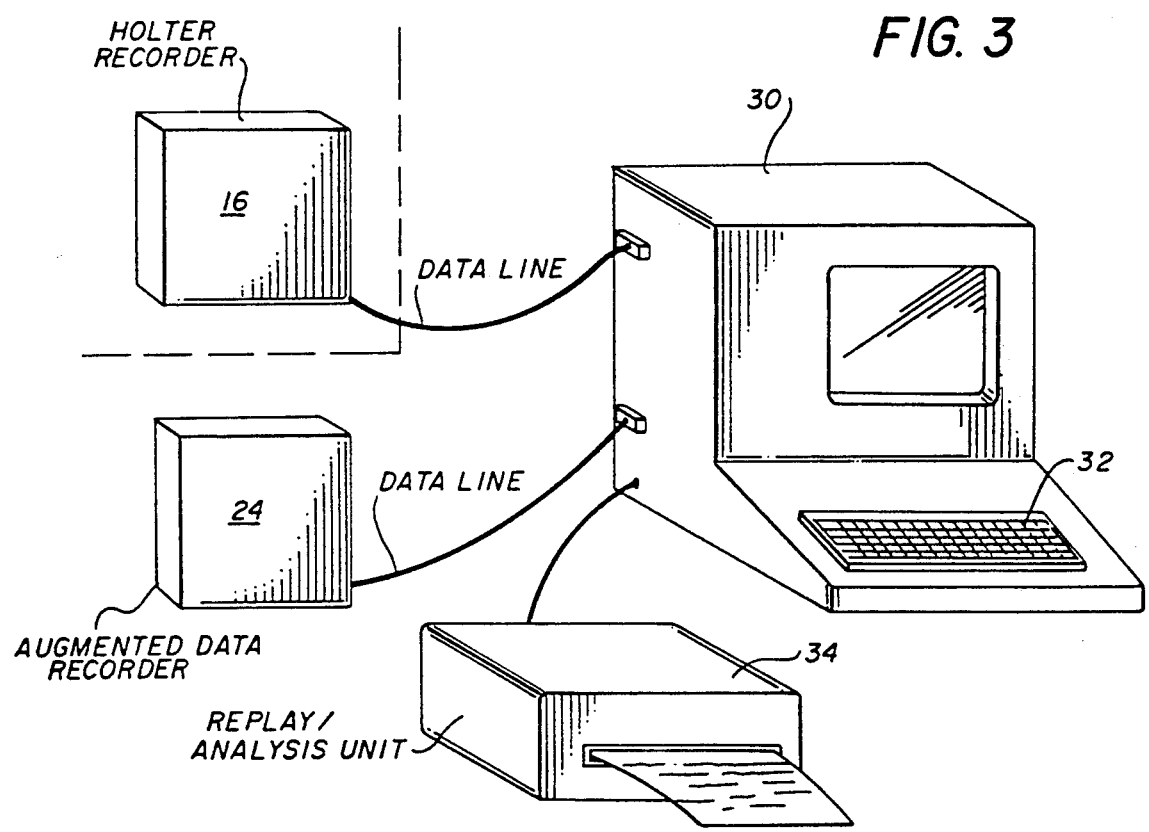

CARDIOVASCULAR MONITORING SYSTEM

BACKGROUND OF THE INVENTION

Continuous, twenty-four hour or longer, electrocardiogram (EKG) monitoring (Holter) systems are widely used in the prior art for diagnosing heart disease. However, the long term prior art EKG systems are concerned only with EKG signals which is a major shortcoming.

There is another much simpler diagnostic means used in the prior art, namely the brief exercise "stress test" in which the EKG signals are recorded during a brief time interval while the patient is exercising strenuously, for example, on a treadmill. However, this latter test is not comprehensive because exercise is only one of a number of stresses that can cause EKG abnormalities.

U.S. Pat. No. 4,830,021 which issued May 16, 1989 to the present inventor describes a locomotor activity monitoring system which includes EKG, and which involves long term monitoring of the patient. The system described in that patent, unlike other prior art cardiac monitoring systems, uses EKG only incidentally and primarily to monitor heart rate.

There are shortcomings in each of the prior art systems referred to above. For example, the Holter System has no detection/recording capability other than time, EKG readings and a patient marker. The patient maintains a time related diary of such events. At best, this approach is qualitative. It is also incomplete, since no data is entered, for example, when the patient is asleep. In essence, there is no objective or recorded evidence of any patient activity.

The cardiac abnormalities which are revealed by the prior art cardiac monitoring systems are equated only to physical activities. However, such cardiac abnormalities may also be revealed by a number of other conditions in the body. Knowledge of these conditions, other than physical activity, which provide detectable cardiac abnormalities is frequently important for determining the proper treatment. As noted above, such knowledge can not be acquired from current cardiac monitoring systems and techniques, and it is an object of the present invention to provide a system which also monitors such other conditions in the body.

It is well known, for example, that inadequate blood supply to the heart may alter a portion of the EKG known as the S.T. segment. It is also well known that the most common cause of inadequate blood supply to the heart is partial closure of one or more arteries by fatty formations. Limited blood flow through a narrowed artery which is inadequate to meet the needs demanded by exercise is the most common cause of such EKG changes. However, normal or slightly affected arteries may produce the same effect due to spasms from emotional upsets which are transmitted to the heart by the nervous system, and which are not detected by the prior art cardiac monitoring systems. The treatment is the case of clogged arteries is normally surgery, but a vastly different treatment is required in the case of arterial spasm cause, for example, by emotional upsets in relatively normal arteries. It follows, therefore, that even the most elaborate and complex EKG recording and analyzing systems in the prior art are incomplete.

SUMMARY OF THE INVENTION

The present invention provides a relatively simple and practical system which detects, records and processes physical and emotional parameters affecting the cardiovascular system of a subject and environmental data, simultaneously with the recording of the subject's EKG data. On replay, should EKG abnormalities be detected, the record can be analyzed for physical activities, emotional stresses, and environmental parameters which could cause such abnormalities. For example, external events known to cause cardiovascular problems include: physical stress; work; exercise; temperature extremes and changes; and fatigue. In addition, there are emotional stresses which also can cause cardiovascular problems, and these include, for example, such emotional stresses as real or perceived danger, anger, conflict, and the like.

BRIEF DESCRIPTION OF THE DRAWINGS

FIG. 3 is a block diagram of a Holter replay/analysis unit which is used to receive data from recorders carried by the subject of FIG. 1.

DETAILED DESCRIPTION OF THE ILLUSTRATED EMBODIMENT

Figure 1:
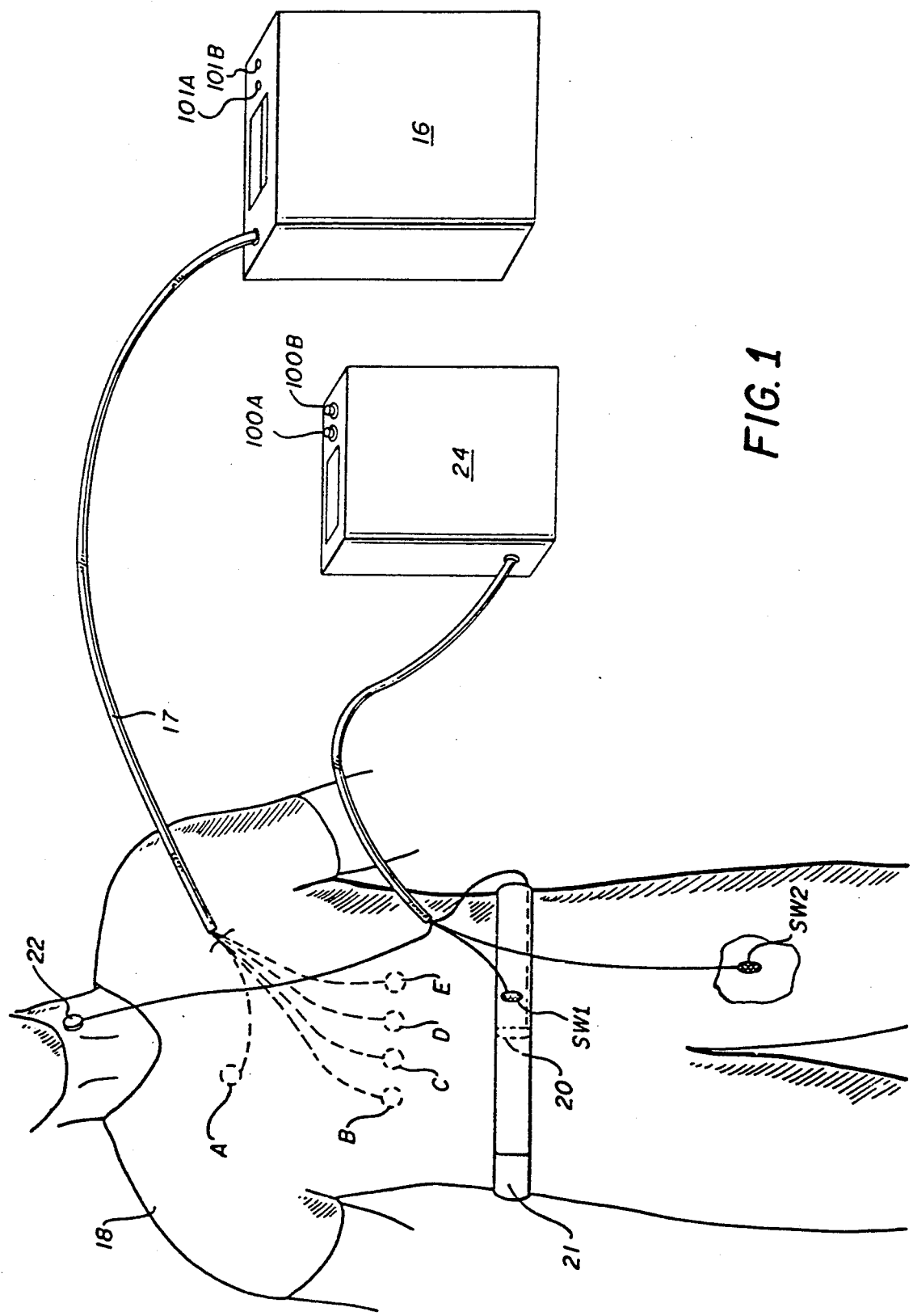
FIG. 1 is a representation of a subject on which various sensors and other instruments are mounted for carrying out desired cardiac monitoring functions.

In order for the Augmented Holter Monitoring (AHM) system of the invention to perform its desired monitoring functions, it is necessary for the subject 18 of FIG. 1 to carry certain sensors, transducers and other equipment. For example, the subject 18 may carry an existing miniature EKG Holter electro-magnetic recorder 16 in one of his shirt pockets. Usual EKG electrodes A–E are mounted on the subject and connected to the Holter recorder 16 over leads 17. The subject 18 also carries a miniature accelerometer 20 on a belt 21, the accelerometer measuring vertical accelerations (Gz) of the subject at his center of gravity. The accelerations (Gz) are converted to vertical forces (Fz) by the system in a manner fully described in U.S. Pat. No. 4,830,021.

Two position sensor switches SW1 and SW2 are also attached to subject 18, one at his waist and the other on his thigh. Switches SW1 and SW2 may be commercially available mercury gravity switches, or other appropriate gravity switches may be used. These switches serve to provide indications of the posture of the subject, specifically whether the subject is standing, sitting or lying down. The operation of such switches is described in some detail in U.S. Pat. No. 4,830,021.

A multiple sensor 22 is mounted on the neck of subject 18. This multiple sensor may include two microphones, as will be described, as well as light and temperature sensors. The light sensor may be a simple photodiode circuit which generates electrical signals indicative of ambient light levels. The temperature sensor may be a thermistor circuit which generates electrical signals indicative of ambient temperature. The sensors 20, 22, as well as switches SW1, SW2 are all connected to a second electro-magnetic recorder 24 which may fit into a second shirt pocket of subject 18, or which may be clipped to the Holter recorder 16. Alternately, recorder 24 may be combined in Holter recorder 16.

Figure 2B:
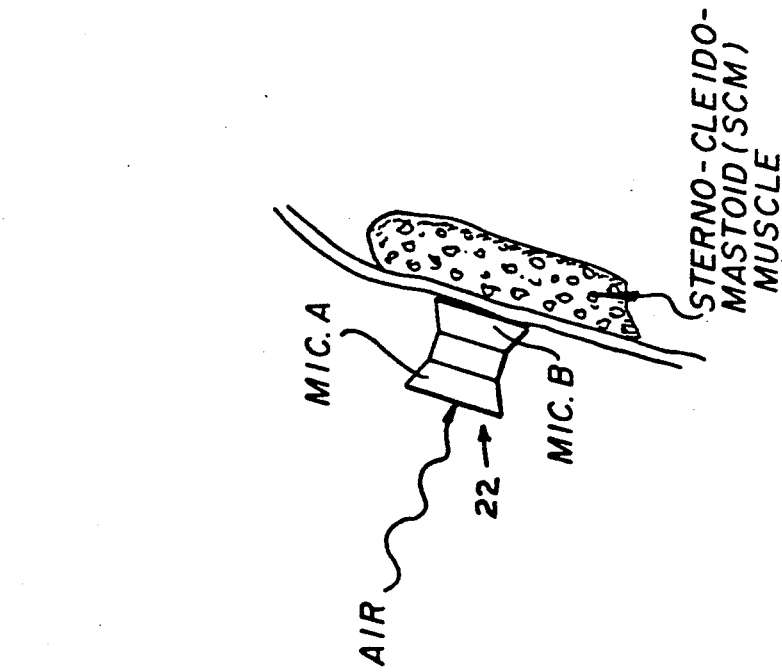
FIGS. 2A and 2B constitute a further representation of the subject shown in FIG. 1, and show the manner in which first and second microphones are mounted on the subject for purposes to be explained, FIG. 2B being a section taken along the line 2B—2B of FIG. 2A.
Figure 2A:
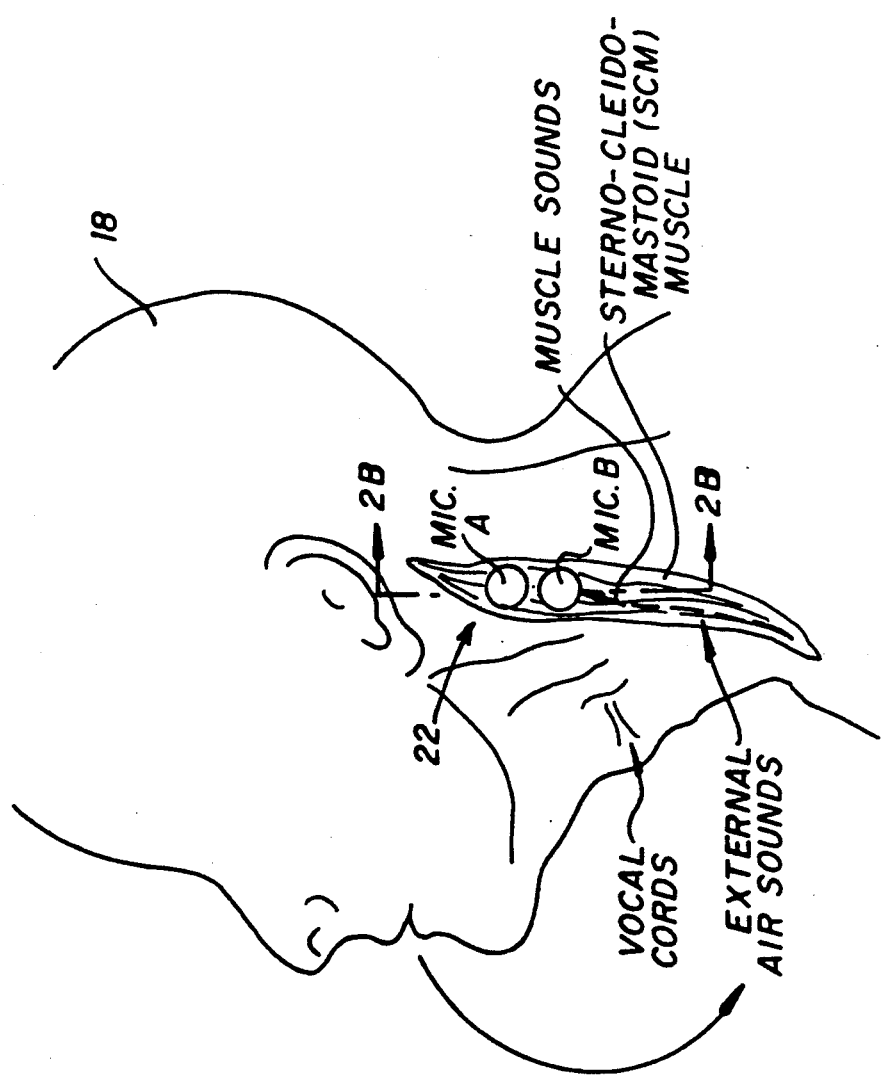

As shown in FIGS. 2A and 2B, multiple sensor 22 includes two microphones designated Mic "A" and Mic "B". Microphones Mic "A" and Mic "B" may be sub-miniature microphones of the dynamic, electret or semiconductor type, and preferably have frequency responses in the range of 20–3000 Hz. Microphone Mic "B" is attached to the neck of subject 18 adjacent to the sterno-cleido-mastoid (SCM) muscle above the collar. Microphone Mic "B" registers strong vibrations from the voice of subject 18 (0.3–3 KHz); and lower frequency vibrations due to muscle contractions of the subject occurring, for example, when the subject is asleep and is experiencing an emotional dream.

Microphone Mic "A", as best shown in FIG. 2B, may be mounted on microphone Mic "B", and the microphones are acoustically isolated from one another. Microphone Mic "A" serves to register the speech of the subject as transmitted through air, and it also registers other sounds transmitted to it by air.

A Holter-type replay/analysis unit 30 is shown in FIG. 3. The recorders 16 and 24 of FIG. 1 are connected to unit 30 during replay, as shown, and data recorded on recorders 16 and 24 is fed into the unit. Unit 30 includes all usual components, including a computer, controls, displays, a keyboard 32 and a printer 34, all of which are needed for processing, and displaying the augmented Holter data from recorders 16 and 24. Analysis of the data from recorder 24 by unit 30 serves to yield substantial amounts of information on the activity of subject 18 of FIG. 1, and of the environment surrounding the subject.

The invention provides, therefore, an improved Augmented Holter monitoring system for detecting, recording and processing parameters affecting the cardiovascular system simultaneously with the recording of EKG data, so that the patient's physical and emotional activities and environmental parameters are taken into account as causing detected EKG abnormalities.

It will be appreciated that while a particular embodiment of the invention has been shown and described, modifications may be made. It is intended in the claims to cover all modifications which come within the true spirit and scope of the invention.

I claim:

1. An augmented Holter cardiovascular monitoring system (AHM) for detecting data related to physical and emotional parameters affecting the cardiovascular system of a subject, and for recording such data simultaneously with the recording of electro cardiogram (EKG) data, including: first sensor means to be mounted on the subject for generating EKG electric signals; second sensor means including a first sound transducer means to be mounted on the subject in a position for detecting internal vibrations of the subject in the 0.3–3 KHz range from the voice of the subject, and a second sound transducer means acoustically isolated from the first transducer means to be mounted on the subject in a position to detect vibrations in the 0.3–3 KHz range from external sources including external voices and for generating electric signals in response thereto; and means connected to said first and second sensor means for continuously recording the electric signals generated thereby on a long term basis.

2. The augmented Holter cardiovascular monitoring system defined in claim 1, in which said first sound transducer means is adapted to be attached to the neck of the subject adjacent to the sterno-cleido-mastoid (SCM) muscle of the subject.

3. The augmented Holter cardiovascular monitoring system defined in claim 1, in which said first sound transducer means also detects low frequency vibrations due to muscle contractions of the subject which occur when the subject is asleep or is experiencing an emotional dream.

4. The augmented Holter cardiovascular monitoring system defined in claim 3, and which includes third sensor means to be mounted on the subject to sense the position of the subject and to generate electric signals related thereto, said recording means being connected to said third sensor means for recording the electric signals generated thereby.

5. The augmented Holter cardiovascular monitoring system defined in claim 2, in which said second sensor means includes light transducer means for generating electric signals indicative of the ambient light level.

6. The augmented Holter cardiovascular monitoring system defined in claim 1, in which said second sensor means includes temperature transducer means for generating electric signals indicative of the ambient temperature.

7. The augmented Holter cardiovascular monitoring system defined in claim 1, and which includes acceleration measuring means to be mounted on the subject for generating electric signals representative of the accelerations of the subject, said recording means being connected to said acceleration measuring means.

8. The augmented Holter cardiovascular monitoring system defined in claim 7, in which said acceleration measuring means is adapted to be mounted on the subject in a position to measure vertical accelerations of the subject substantially at the center of gravity of the subject.

9. The augmented Holter cardiovascular monitoring system defined in claim 1, and which includes a replay/analysis means connected to said recording means for processing data recorded on said recording means.

10. A method for detecting an monitoring data related to physical and emotional parameters affecting the cardiovascular system of a subject and for recording such data on a long term continuous basis, comprising the following steps: mounting a first sensing means on the subject for generating EKG electric signals; mounting a first transducer means on the subject in a position for detecting internal vibrations in the 0.3–3 KHz range from the voice of the subject and for generating electric signals in response thereto; mounting a second sound transducer means on the subject acoustically isolated from the first transducer means in a position to detect vibrations from external sources including external voices and for generating electric signals in response thereto; and continuously recording the electric signals from said first sensor means and from said first and second sound transducer means on a long term basis.

11. The method defined in claim 10, in which the first transducer means is attached to the neck of the subject adjacent to the sterno-cleido-mastoid (SCM) muscle of the subject to enable said first sound transducer to detect low frequency vibrations due to muscle contractions of the subject which occur when the subject is asleep and is experiencing an emotional dream.

12. The method defined in claim 10, and which includes the step of mounting a second sensor means on the subject to sense the position of the subject and to generate electric signals related thereto, and for continuously recording the electric signals generated by said second sensor means on a long term basis.

13. The method defined in claim 10, in which includes mounting a light transducer means on the subject for generating electric signals indicative of the ambient light, and continuously recording the electric signals generated by said light transducer means on a long term basis.

14. The method defined in claim 10, in which includes mounting a temperature transducer means on the subject for generating electric signals indicative of the ambient temperature, and recording the electric signals from said temperature transducer means continuously on a long term basis.

15. The method defined in claim 10, in which includes mounting an acceleration measuring means on the subject for generating electric signals representative of accelerations of the subject, and continuously recording the electric signals generated by said acceleration means on a long term basis.

16. The method defined in claim 15, and which comprises mounting the acceleration measuring means on the subject in a position to measure vertical accelerations of the subject substantially at the center of gravity of the subject.

17. The method defined in claim 10, in which includes the step of processing the recorded electric signals from said first sensor means and from said first and second sound transducer means.

* * * * *